United States Patent
Kim et al.

(10) Patent No.: US 8,023,014 B2
(45) Date of Patent: Sep. 20, 2011

(54) METHOD AND APPARATUS FOR COMPENSATING IMAGE SENSOR LENS SHADING

(75) Inventors: Dong-yong Kim, Gyeonggi-do (KR); Yo-Hwan Noh, Gyeonggi-do (KR)

(73) Assignee: Mtekvision Co., Ltd., Seoul (KR)

( * ) Notice: Subject to any disclaimer, the term of this patent is extended or adjusted under 35 U.S.C. 154(b) by 1204 days.

(21) Appl. No.: 11/573,885

(22) PCT Filed: Dec. 7, 2004

(86) PCT No.: PCT/KR2004/003199
§ 371 (c)(1),
(2), (4) Date: Feb. 16, 2007

(87) PCT Pub. No.: WO2006/019209
PCT Pub. Date: Feb. 23, 2006

(65) Prior Publication Data
US 2008/0043117 A1    Feb. 21, 2008

(30) Foreign Application Priority Data
Aug. 18, 2004 (KR) .......... 10-2004-0065165

(51) Int. Cl.
H04N 9/64 (2006.01)
H04N 5/225 (2006.01)
H04N 5/228 (2006.01)

(52) U.S. Cl. ....................... 348/251; 348/335

(58) Field of Classification Search ............. 348/223.1, 348/224.1, 229.1, 246, 247, 249–251, 255
See application file for complete search history.

(56) References Cited

U.S. PATENT DOCUMENTS

| 6,028,957 | A | 2/2000 | Katori et al. |
| 6,084,983 | A | 7/2000 | Yamamoto |
| 6,195,469 | B1 | 2/2001 | Nishioka et al. |
| 6,239,137 | B1 | 2/2003 | Sato et al. |
| 694,795 | A1 | 10/2003 | Tsuruoka et al. |
| 7,317,482 | B2* | 1/2008 | Sato et al. ............ 348/251 |
| 7,408,576 | B2* | 8/2008 | Pinto et al. ........... 348/251 |
| 7,432,966 | B2* | 10/2008 | Sato et al. ............ 348/251 |
| 2002/0008760 | A1* | 1/2002 | Nakamura ........... 348/222 |
| 2002/0094131 | A1* | 7/2002 | Shirakawa .......... 382/274 |

(Continued)

*Primary Examiner* — David Ometz
*Assistant Examiner* — Carramah J Quiett
(74) *Attorney, Agent, or Firm* — Birch, Stewart, Kolasch & Birch, LLP

(57) ABSTRACT

The invention relates to a method and apparatus for compensating the lens shading phenomenon in image sensor. The invention first stores an inputted compensation reference value, identifies a center pixel using digital image signals received sequentially in correspondence to each pixel from a sensor, generates analysis data corresponding to each pixel, generates and stores block compensation values for blocks grouped according to the distance from the center pixel, calculates the distance from a compensation target pixel to the center pixel, calculates a compensation value corresponding to the compensation target pixel using the block compensation value corresponding to the distance, and generates for output correction pixel data by aggregating analysis data and the compensation value corresponding to the compensation target pixel. Thus, the invention allows the maintaining of colors as close as possible to the original through the respective compensation of RGB which takes into consideration the respective characteristics of the color filters and through the respective compensation of gain and level for the disparity in transmissivity according to position.

15 Claims, 12 Drawing Sheets

U.S. PATENT DOCUMENTS

| | | | |
|---|---|---|---|
| 2002/0135688 A1* | 9/2002 | Niikawa | 348/251 |
| 2003/0156190 A1* | 8/2003 | Sato et al. | 348/94 |
| 2004/0105016 A1* | 6/2004 | Sasaki | 348/222.1 |
| 2004/0257454 A1* | 12/2004 | Pinto et al. | 348/222.1 |
| 2005/0041806 A1* | 2/2005 | Pinto et al. | 380/210 |
| 2008/0291302 A1* | 11/2008 | Noh | 348/251 |

* cited by examiner

FIG. 10
Level adjustment
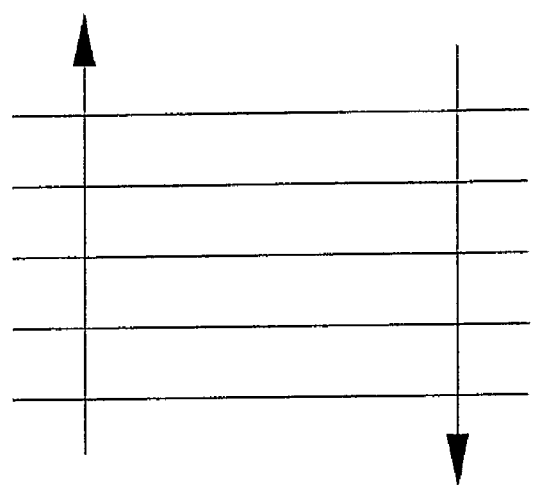
Increase level     Decrease level
Gain adjustment
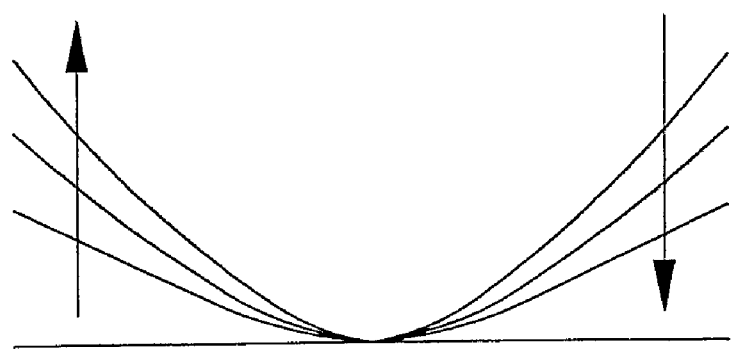
Increase gain     Decrease gain

METHOD AND APPARATUS FOR COMPENSATING IMAGE SENSOR LENS SHADING

CROSS REFERENCE TO RELATED APPLICATIONS

This application is a U.S. National Application of International Application PCT Application No. PCT/KR2004/003199 filed on Dec. 7, 2004, which claims the benefit of priority from Korean Patent Application No. 10-2004-0065165 filed on Aug. 18, 2004. The disclosures of International Application PCT Application No. PCT/KR2004/003199 and Korean Patent Application No. 10-2004-0065165 are incorporated herein by reference.

FIELD OF THE INVENTION

The invention relates to a method and apparatus for compensating the lens shading phenomenon in image sensor, more particularly to a method and apparatus for compensating the lens shading phenomenon in image sensor where the quality of original images is maintained by correcting the reduction in signal amplitude according to the position of the pixels.

BACKGROUND OF THE INVENTION

Portable devices with image sensor (e.g. digital cameras, mobile communication terminals, etc.) have recently been developed and are currently in the market. Image sensor comprises an array of tiny photosensitive diodes known as pixels or photosites. The pixels themselves usually do not extract color from light, but convert photons into electrons from a wide spectrum band. To record color images with a single sensor, the sensor is filtered so that different pixels receive lights with different colors. This type of sensor is known as a color filter array, or CFA. Different color filters are disposed across the sensor in a predefined pattern.

The most common pattern is the Bayer color filter array developed by Kodak. The CFA of a color image generally follows a Bayer pattern. In other words, a half of the total number of pixels is green (G), and two quarters of the total number are assigned red (R) and blue (B). To obtain color information, the color image pixels are formed as a repetitive pattern of red, green, or blue filters, 2×2 arrays in the case of a Bayer pattern, for example.

The Bayer pattern is based on the premise that the human eye derives most of the luminance data from the green content of a scene. Therefore, an image with a higher resolution may be generated when more of the pixels are made to be green, compared to when an equal number of red, green, and blue pixels alternate.

However, the conventional image sensor on recently marketed portable devices had a problem of image distortion due to the geometric pattern of the pixel array composition. This is because of its small outer lens and high f number.

FIG. 1 is a diagram illustrating the disparity in transmissivity, and FIG. 2 is a graph illustrating the change in signal amplitude according to the distance from the center.

As illustrated in FIG. 1, the pixels in the central part of the image sensor and the pixels in the outer perimeter are exposed to the light source from different positions. These minute differences in position cause differences in illumination, and differences in illumination affect color because of differences in light frequency and refractive ratio.

Consequently, color distortion and reduction in signal amplitude dependant on the position of the pixels inevitably occur, which cause degradation in the quality of original images.

DETAILED DESCRIPTION OF THE INVENTION

Technical Problem

Therefore, it is an object of the invention to solve the problems described above and to provide a method and apparatus for compensating the lens shading phenomenon in image sensor which prevent degradation of original image.

It is another object of the invention to provide a method and apparatus for compensating the lens shading phenomenon in image sensor which allows overall illumination compensation and compensation for the color distortion of the respective color filters of RGB and the reduction in signal amplitude according to pixel position.

It is a further object of the invention to provide a method and apparatus for compensating the lens shading phenomenon in image sensor with which colors as close as possible to the original may be maintained through the respective compensation of RGB which takes into consideration the respective characteristics of the color filters and through the respective compensation of gain and level for the disparity in transmissivity according to position.

It is another object of the invention to provide a method and apparatus for compensating the lens shading phenomenon in image sensor in which the amount of data to be processed can be minimized when correcting the original image.

It is yet another object of the invention to provide a method and apparatus for compensating the lens shading phenomenon in image sensor which can correct the position of the center pixel of the shading image.

Technical Solution

According to an aspect of the invention for realizing the above objectives, a method is provided of compensating the lens shading phenomenon in image sensor, comprising: storing an inputted compensation reference value; identifying a center pixel using digital image signals received sequentially in correspondence to each pixel from a sensor, and generating analysis data corresponding to each pixel; generating and storing block compensation values for blocks grouped according to the distance from the center pixel; (a) calculating the distance from a compensation target pixel to the center pixel; (b) calculating a compensation value corresponding to the compensation target pixel using the block compensation value corresponding to the distance; (c) generating correction pixel data by aggregating analysis data and the compensation value corresponding to the compensation target pixel; and (d) outputting the correction pixel data to an interpolation part.

The steps (a) to (d) may sequentially be performed with regard to the each pixel received sequentially.

The compensation reference value may be settings for level and gain, and the block compensation values may be two compensation values generated using the differences between the analysis data of the starting and ending positions of each block, respectively, and the compensation reference value.

The step (b) may comprise: selecting a block corresponding to the distance; extracting two compensation values corresponding to the selected block; generating a linear equation which passes the two compensation values and has the distance as a variable; and calculating the compensation value corresponding to the distance using the linear equation.

In the method of compensating the lens shading phenomenon in image sensor, the compensation values for RGB respectively may be calculated using the setting for gain when the degrees of intensity are equal for the RGB of the center pixel, and the compensation values for RGB respectively may be calculated using the settings for level and gain when the degrees of intensity are unequal for the RGB of the center pixel.

The digital image signals may be Bayer pattern image signals.

The block compensation values may be generated based mainly on the luminance component with the green (G) pixel as the standard.

In the method of compensating the lens shading phenomenon in image sensor, the center pixel may be identified by first detecting the positions of the two pixel values with the highest brightness values on the vertical and horizontal lines passing a pixel, and then, by using the deviations between the positions of the pixel values and the position of the center value of the pixel array, moving the center of the pixel array to the center of the shading image.

According to another aspect of the invention, an image processor is provided for compensating the lens shading phenomenon in image sensor, in an imaging device consisting of a sensor, the image processor, and a display, comprising: a correction processing part which identifies a center pixel using digital image signals received sequentially in correspondence to each pixel from the sensor, generates analysis data corresponding to each pixel, generates block compensation values for blocks grouped according to distance from the center pixel using the compensation reference value, calculates the distance from a compensation target pixel to the center pixel, calculates the compensation value corresponding to the correction target pixel using the block compensation value corresponding to the distance, and generates and outputs correction pixel data by aggregating the analysis data and the compensation value corresponding to the compensation target pixel; an interpolation processing part which performs interpolation processing using the correction pixel data; and a latter processing part which enables the interpolated correction pixel data to be displayed via the display.

According to a preferred embodiment of the invention, a lens shading compensation device is provided, for compensating the lens shading phenomenon in image sensor, comprising: a pixel value analysis part which identifies a center pixel using digital image signals received sequentially in correspondence to each pixel from a sensor which photographs a subject and which generates digital image signals, and generates analysis data corresponding to each pixel; a table generator part which, by using the analysis data and pre-configured compensation reference value, generates compensation values corresponding to each block consisting of a plurality of pixels; a pixel position calculator part which calculates the distance between the center pixel and a compensation target pixel; a compensation curve generator part which calculates the compensation value of the compensation target pixel by extracting two or more compensation values generated to correspond to the calculated distance by the table generator part; and a correction execution part which generates and outputs compensation pixel data by aggregating analysis data and the compensation value corresponding to the compensation target pixel.

The lens shading compensation device may be positioned between the sensing part and the interpolation processing part, and the correction execution part may output the compensation pixel data to the interpolation processing part.

The compensation curve generator part may generate compensation values corresponding to the distance between the compensation target pixel and the center pixel by a set of procedures comprising: selecting a block corresponding to the distance; extracting two compensation values corresponding to the selected block; generating a linear equation which passes the two compensation values and has the distance as a variable; and calculating the compensation value corresponding to the distance using the linear equation.

BRIEF DESCRIPTION OF THE DRAWINGS

FIG. 10 is a diagram illustrating the method of adjusting level and gain according to a preferred embodiment of the invention.

LIST OF REFERENCE NUMBERS FOR MAJOR COMPONENTS

Figure 1:
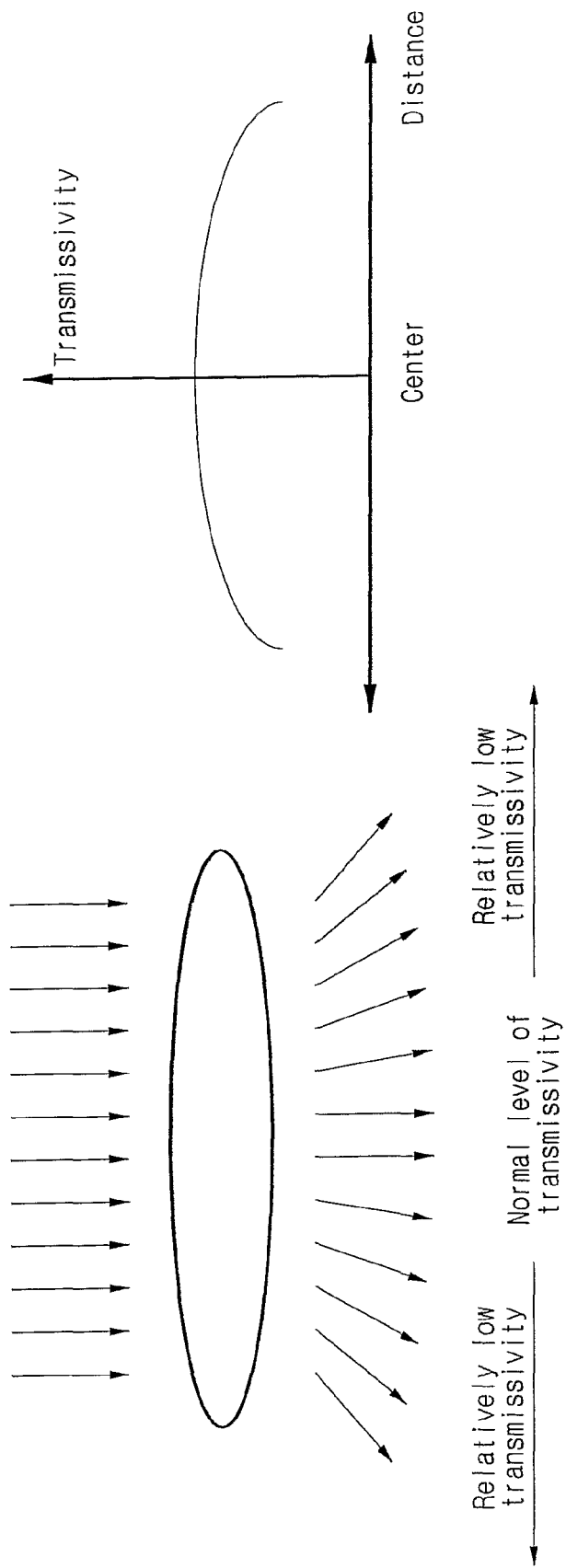
FIG. 1 is a diagram illustrating the disparity in transmissivity.
Figure 2:
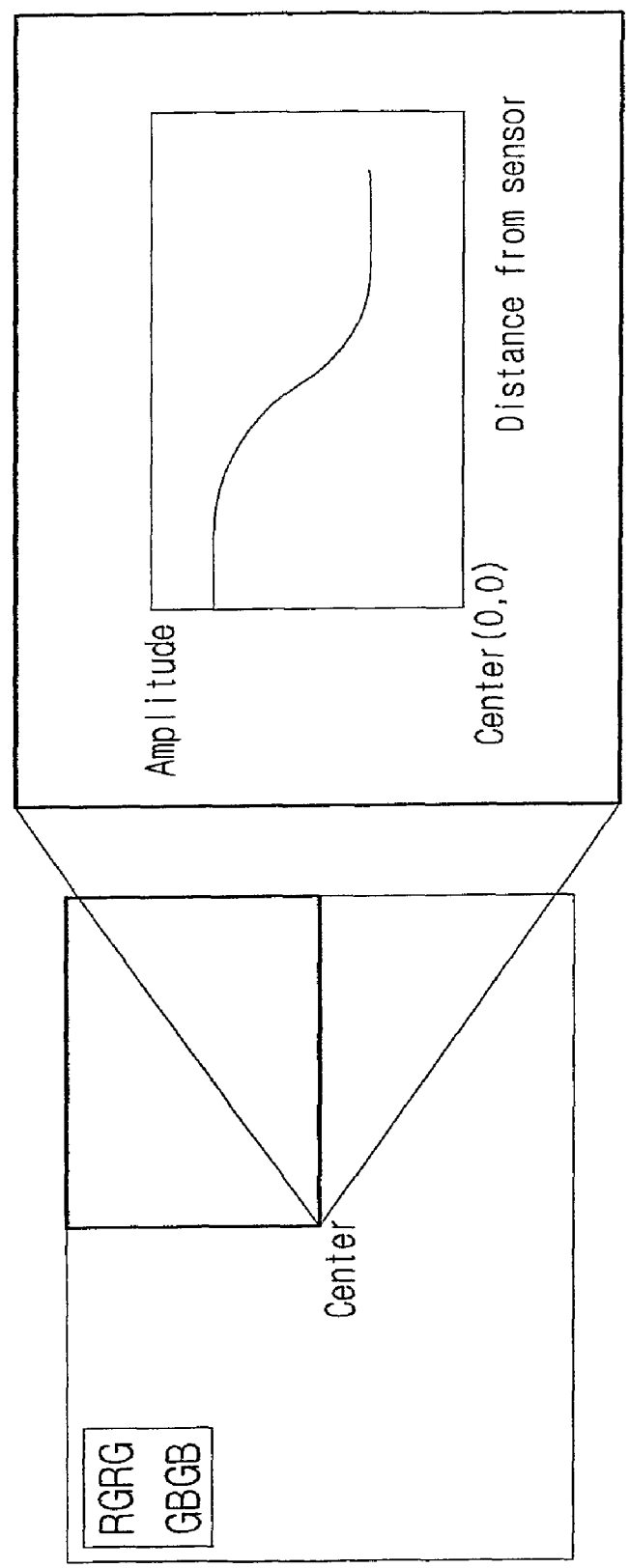
FIG. 2 is a graph illustrating the change in signal amplitude according to the distance from the center.

130: correction processing part
210: pixel value analysis part
220: table generator part
230: pixel position calculator part
240: compensation curve generator part
250: correction execution part

EMBODIMENTS

To fully understand the invention, the operational advantages of the invention, and the objectives realized through the use of the invention, the accompanying drawings and the description included therein must be examined which illustrate preferred embodiments of the invention.

Hereinafter, preferred embodiments of the invention will be described in more detail with reference to the accompanying drawings. In the descriptions, identical components are rendered the same reference number regardless of the figure number to allow an overall understanding of the invention.

Figure 3:
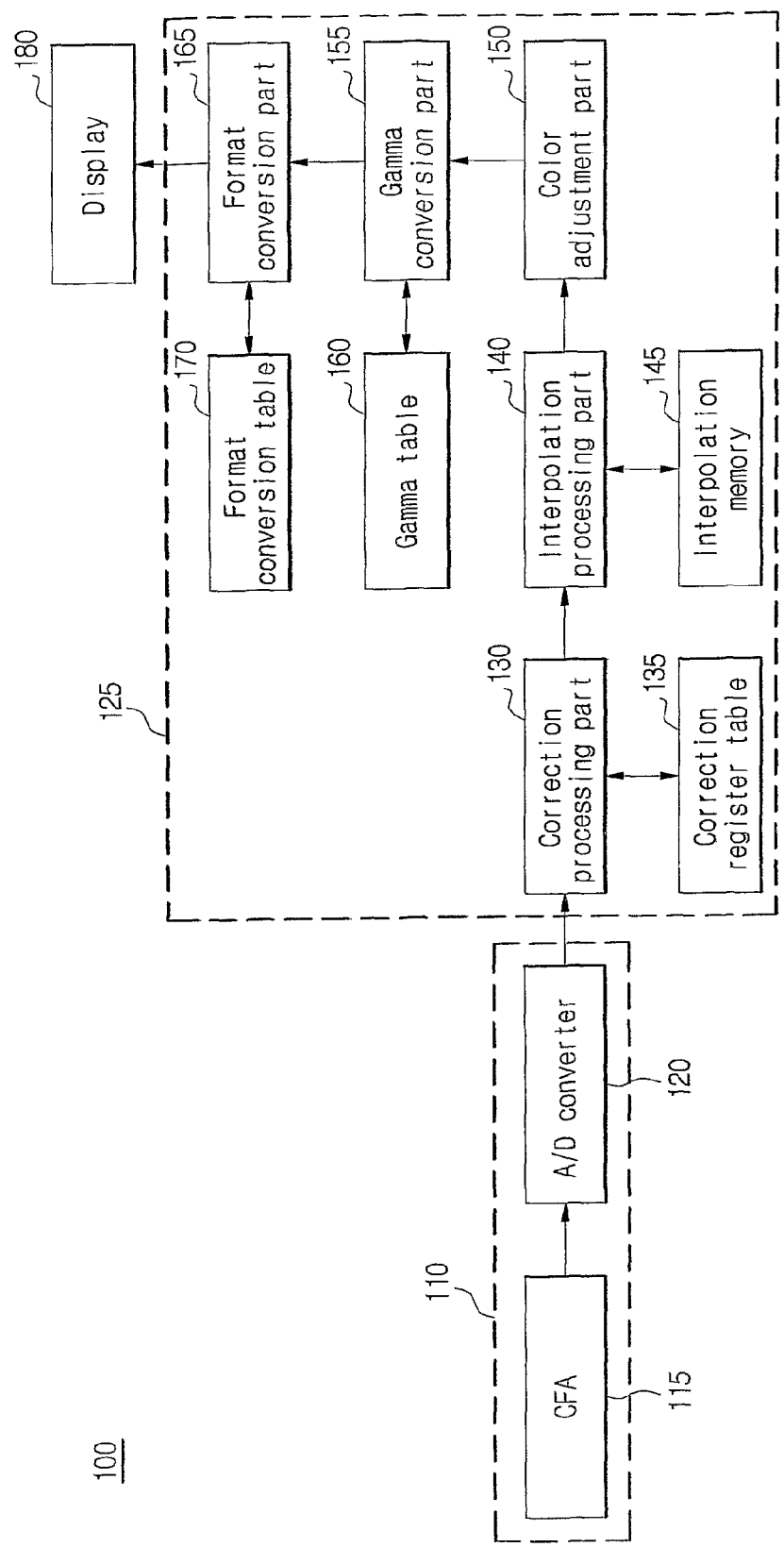
FIG. 3 is a schematic drawing illustrating the composition of an imaging device according to a preferred embodiment of the invention.

FIG. 3 is a schematic illustrating the composition of an imaging device according to the preferred embodiment of the invention.

Referring to FIG. 3, the imaging device 100 according to the invention comprises a sensor 110, an image processor 125, and a display 110. Of course, an input key or memory etc. may further be included, but explanation on these components is omitted, as they are irrelevant to the essentials of the invention.

The sensor 110 comprises a CFA (color filter array) 115 and an A/D converter 120. Of course, a lens may further be included, as mentioned above.

The CFA 115 converts the optical signal of the subject to an electronic signal for output. Here, the CFA 115 uses a Bayer pattern, which is advantageous in terms of resolution, and an image signal having a color data is outputted for each pixel, i.e. an image signal having R data only is outputted from a pixel associated with a R pattern, an image signal having G data only is outputted from a pixel associated with a G pattern, and an image signal having B data only is outputted from a pixel associated with a B pattern. The value of each pixel obtained through the Bayer patterned CFA 115 is interpolated (for example, by inferring the mixing color data after averaging the values of the two pixels to the left and to the right or the four pixels to the left, to the right, above, and below, etc.) to yield perfect color data. The interpolation is performed by the interpolation processing part 140.

The A/D converter 120 converts the image signals converted by the CFA 115 to digital signals and transfers them to the correction processing part 130.

The image processor 125 comprises the correction processing part 130, a correction register table 135, the interpolation processing part 140, interpolation memory 145, a color adjustment part 150, a gamma conversion part 155, a gamma table 160, a format conversion part 165, and a format conversion table 170. In addition, the image processor 125 may include a horizontal synchronous signal (Hsync), vertical synchronous signal (Vsync), and a timing generator part (not shown) which generates various timing signals from the pixel clock (PCLK), used in the operation of the CFA 115.

The correction processing part 130 analyzes the luminance of each image signal, analyzes the gain and level of RGB, respectively, identifies the center pixel of the shading image, and transfers the original image signal corrected in a predetermined manner to the interpolation processing part 140. Here, the user may manually define the desired gain and level values. The gain is for modifying the RGB intensity within a frame, as there may be a disparity in the RGB intensities because of the disparity in light transmissivity between the center pixels and the outer pixels. The level is related to the brightness of each pixel; for instance, if the level of all pixels within a frame is 10, then it may be said that the brightness of the entire screen is 10. Thus, the correction processing part 130 according to the invention has the effect of preventing the degradation in quality of original images by correcting the image signals of all pixels within a frame to correspond to the gain and level settings established by the user. The composition and function of the correction processing part 130 is described in detail with reference to FIG. 4.

The correction register table 135 is generated by the luminance component and is generated with regard to any value among RGB and the center pixel of the shading image. For example, with regard to G, under the premise that it accounts for the highest number among RGB values and that the human eye derives most of the luminance data from the green content of a scene, the differences between the G value and the other values (i.e. the R value and the B value) are calculated, and the differences are configured to equal user settings. The correction register table 135 has entries in terms of blocks formed according to the distance from the center pixel (e.g. 16 pixels, 32 pixels, 64 pixels, etc.). There is a problem in that the wider the interval which forms a block, the more inaccurate is the shading due to block value boundary problems. In practice, using 16 pixels allows accurate shading correction but requires a large register size, so that 32 pixels are generally used. The reason for forming blocks in constant pixels is to omit division operations during shading compensation because shift operations are performed. The correction register table 135 illustrated in FIG. 3 may be a storage area in which to store a generated correction register table.

The interpolation processing part 140 generates RGB pixel signals for each pixel. When the image signals outputted from the CFA 115 have a Bayer pattern, green (G) or blue (B) pixel signals cannot be obtained from pixels associated with red (R). Thus, the interpolation processing part 140 can generate green (G) or blue (B) pixel signals from a red (R) color filter pixel through interpolation operations. For this, the pixel signals of surrounding pixels are temporarily recorded in the interpolation memory 145, and the interpolation processing part 140 performs interpolation operations using the pixel signals of the surrounding pixels temporarily recorded in the interpolation memory 145.

The color adjustment part 150 is a means to adjust the shade (e.g. a bluish shade, etc.), and the gamma conversion part 155 is a means to adjust an image to fit device characteristics (gamma characteristics) for output to the display 180 (e.g. LCD, CRT, etc). A conversion table is stored in the gamma table 160 for conversion to the gamma characteristics of the screen output device in the display 180.

The format conversion part 165 is a means for conversion to a screen signal format suitable to the display 180, which converts pixel signals to digital component formats such as NTSC, YUV, or YcbCr, etc. for output. The format conversion table 170 is a table for conversion to display signal formats such as NTSC or YUV, etc.

Figure 4:
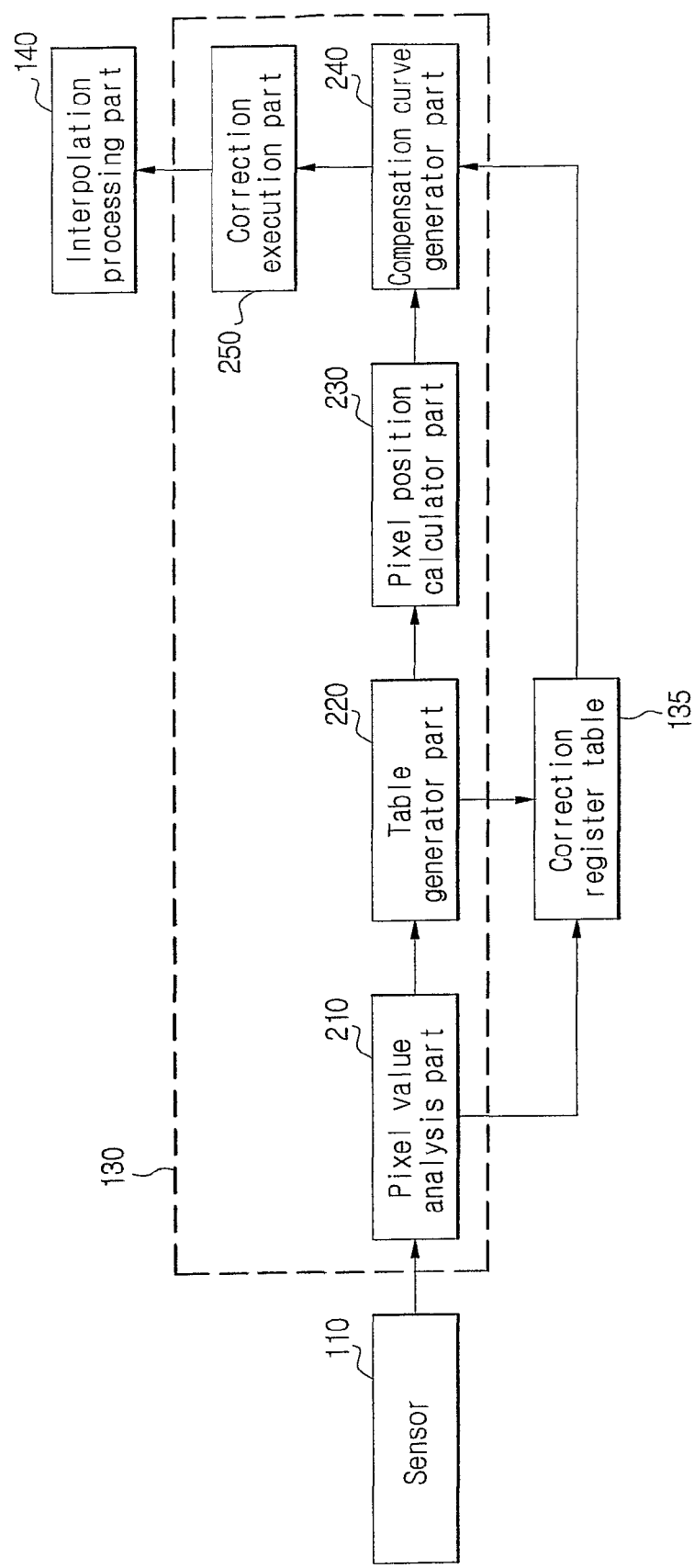
FIG. 4 is a schematic drawing illustrating in detail the composition of the correction processing part 130 according to a preferred embodiment of the invention.
Figure 5:
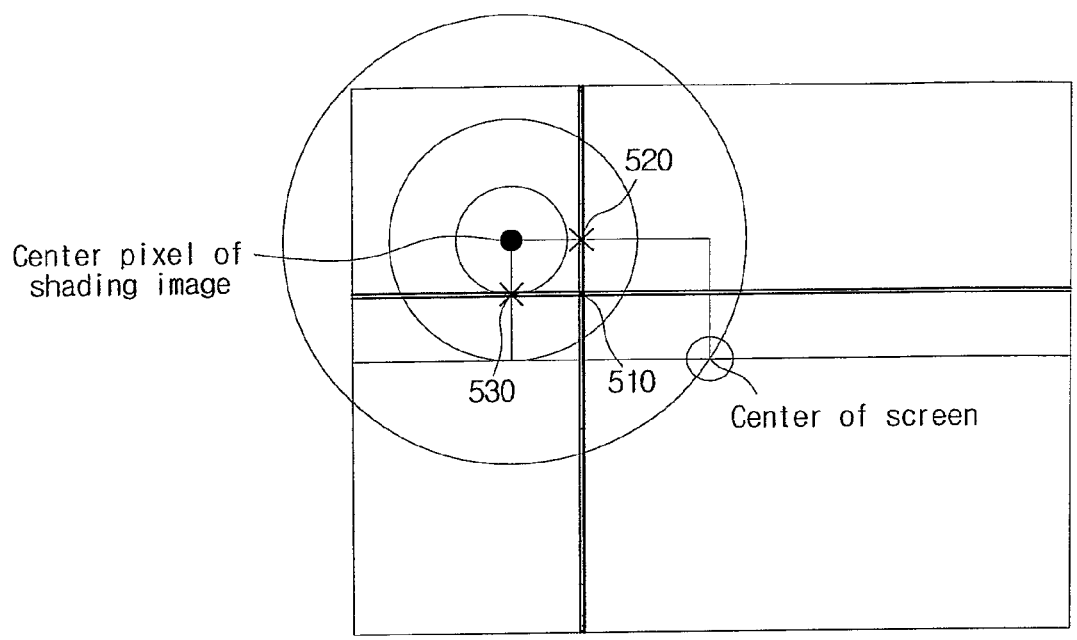
FIG. 5 is a diagram illustrating the method of identifying the center pixel according to a preferred embodiment of the invention.

FIG. 4 is a schematic illustrating in detail the composition of the correction processing part 130 according to a preferred embodiment of the invention, and FIG. 5 is a diagram illustrating the method of identifying the center pixel according to a preferred embodiment of the invention.

Referring to FIG. 4, the correction processing part 130 comprises the pixel value analysis part 210, the table generator part 220, the pixel position calculator part 230, the compensation curve generator part 240, and the correction execution part 250.

The pixel value analysis part 210 uses the digital image signals received per line from the sensor 110 to analyze the luminance data, gain data, and level data corresponding to each pixel, and performs the function of identifying the center pixel of the shading image. The analysis of the digital image signal by the pixel value analysis part 210 may be performed for each line, for the entire frame, or for the center line only. Since the correction processing part 130 according to the invention performs analysis on the image signals before interpolation, the amount of data to be analyzed can be reduced to ⅓. Obviously, other options may be applied in correspondence to the bit data (e.g. 10 bits or 8 bits) of the image signals before interpolation for the pixel value analysis part 210 according to the invention. The method by which the pixel value analysis part 210 analyzes digital image signals may be described briefly as follows. The pixel value analysis part 210 can perform analysis for RGB respectively, since the inputted digital image signals are inputted in a RGB Bayer pattern. First, the center pixel of the shading image is identified from a white image. This is to align to the accurate center when the center of the shading image is not the center of the pixel array. It is also because when the center of the shading image is not aligned, distortion of the image may occur. When the center pixel of the shading image is identified, the position of the center pixel is stored in the correction register table 135, and a shading compensation image is generated about the center pixel. Referring to the diagram of FIG. 5, the method of identifying the center pixel may be described briefly as follows. First, the pixel value analysis part 210 detects the positions of the two pixel values 520, 530 with the highest brightness values on the vertical and horizontal lines passing a pixel 510. Then, using the deviations between the positions of the pixel values 520, 530 and the position of the center value of the pixel array, the center of the pixel array is moved to the center of the shading image, so that the center pixel is identified.

This is done by comparing the pixel value of each unit pixel in the line containing the center pixel value of the pixel array with the center value of the pixel array, and moving the center of the shading image if the pixel value of the unit pixel is greater.

The table generator part 220 generates and stores the correction register table which contains the analysis results of the pixel value analysis part 210 (e.g. the gain and level values, luminance values etc. of RGB, respectively) and/or compensation values. The compensation values may, for example, be generated to correspond to block units (e.g. the starting and ending positions of a certain block, etc). Settings predefined by the user (e.g. gain and level settings) and the analysis results of the pixel value analysis part 210 may be used to generate compensation values, and these settings may be stored in the correction register table 135 or a separate storage part (not shown). It is obvious that that the table generator part 220 may be included within the pixel value analysis part 210.

The pixel position calculator part 230 calculates the distance between each pixel and the center pixel identified by the pixel value analysis part 210. The correction processing part 130 counts the image signals coming from the horizontal and vertical directions (this may be performed by the pixel value analysis part 210, for example, or a separate counting means), and the count numbers indicate the position of the corresponding pixel. This may be used by the pixel position calculator part 230 to calculate the distance between each pixel and the center pixel, and the distances between the pixels and the center pixel are grouped as blocks (see FIG. 8 and FIG. 10). Also, the count numbers allow the analysis data stored in the correction register table 135 to be coupled with each pixel.

The compensation curve generator part 240 extracts the compensation values stored in the correction register table 135 that are coupled with the count numbers, and calculates the compensation value for a certain pixel. The entries of the correction register table 135 are configured to correspond to the unit block of the pixel array (e.g. 16 pixel, 32 pixel, 64 pixel), and the compensation values within a unit block may be generated using entries from two tables (e.g. the compensation value of the block starting position and the compensation value of the block ending position). This is explained in detail with reference to FIG. 6 and FIG. 8.

The correction execution part 250 aggregates for each pixel the analysis result from the pixel value analysis part 210 and the calculated compensation value from the compensation curve generator part 240 to generate correction pixel data, and transfers the generated correction pixel data to the interpolation processing part 140. Thus, the corrected image with the shading phenomenon removed is transferred to the interpolation processing part 140.

Figure 6:
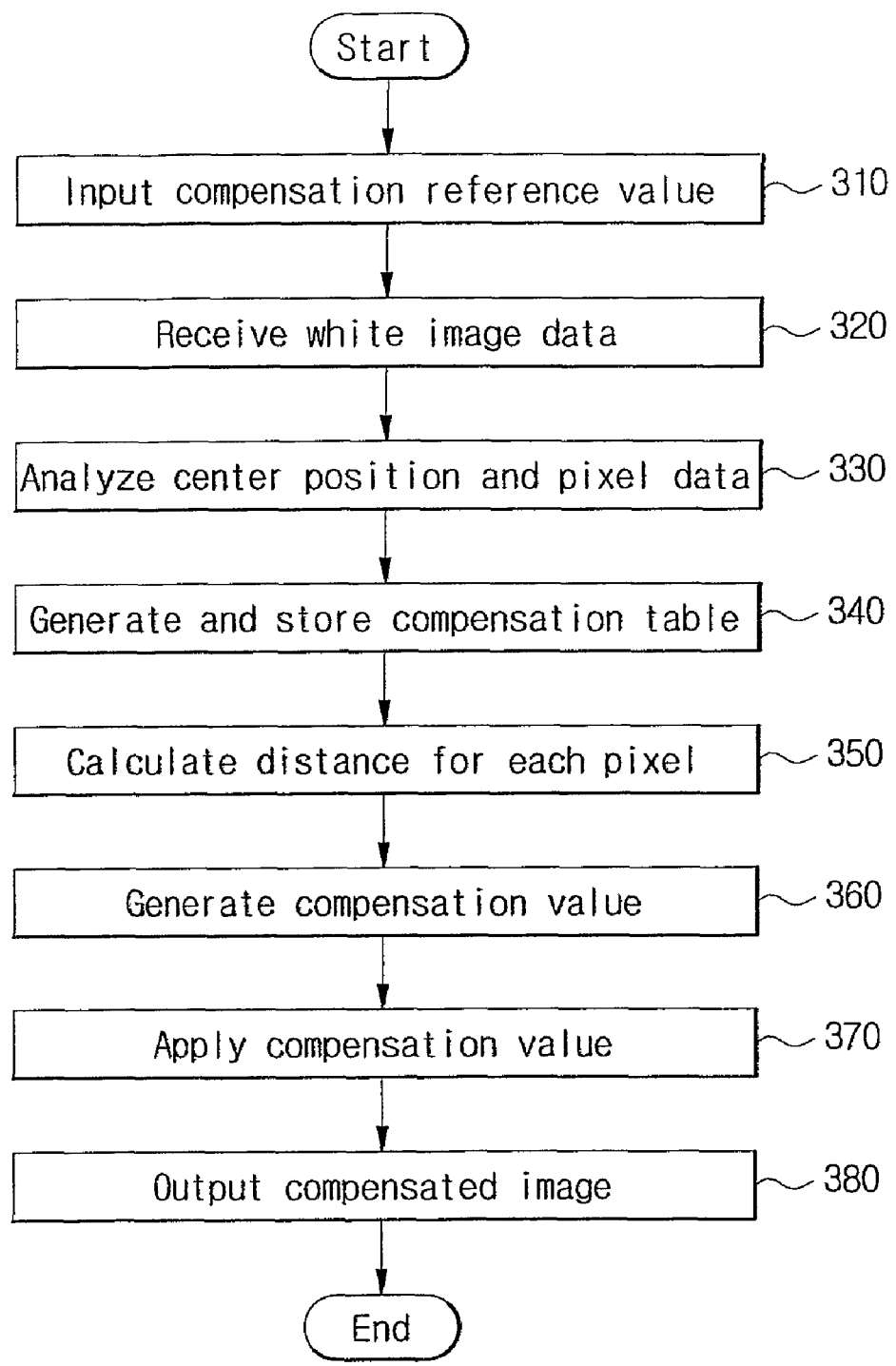
FIG. 6 is a flowchart illustrating the method of compensating the lens shading phenomenon according to a preferred embodiment of the invention.
Figure 7:
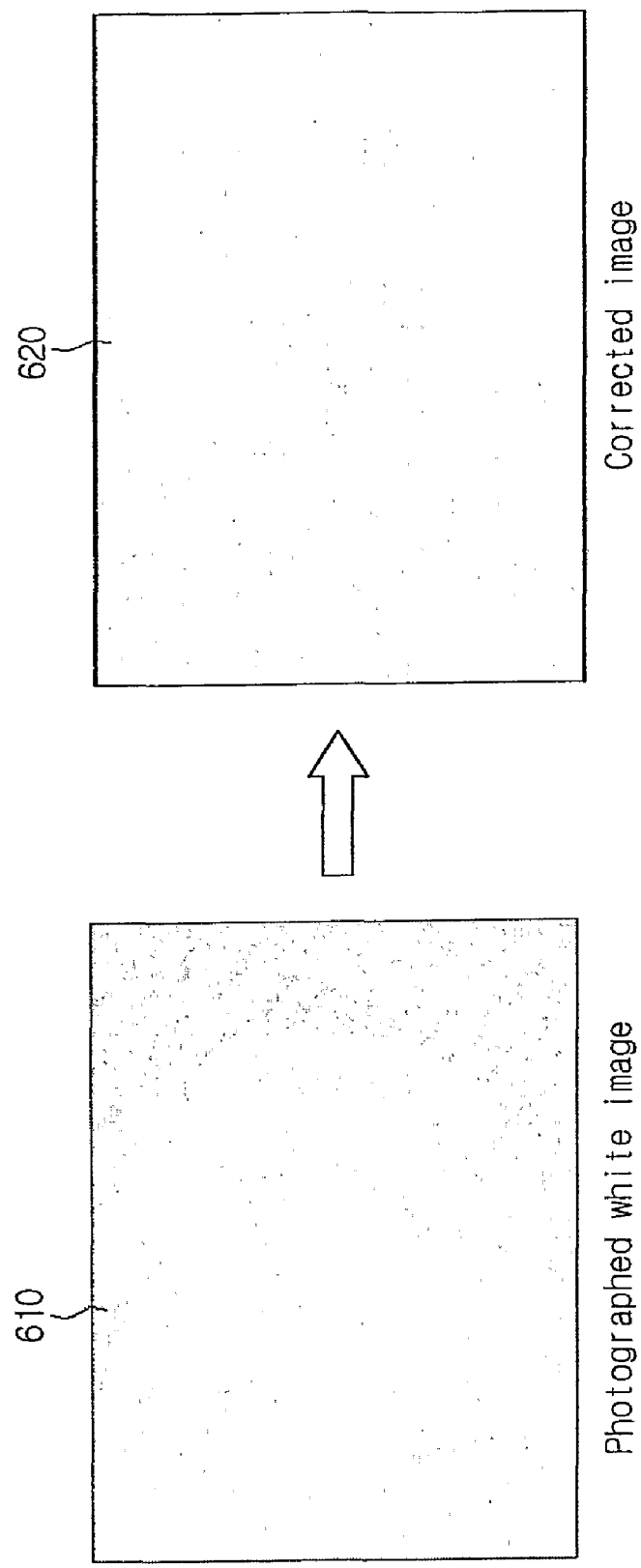
FIG. 7 is a diagram illustrating by example a white image and a corrected image according to a preferred embodiment of the invention.
Figure 8:
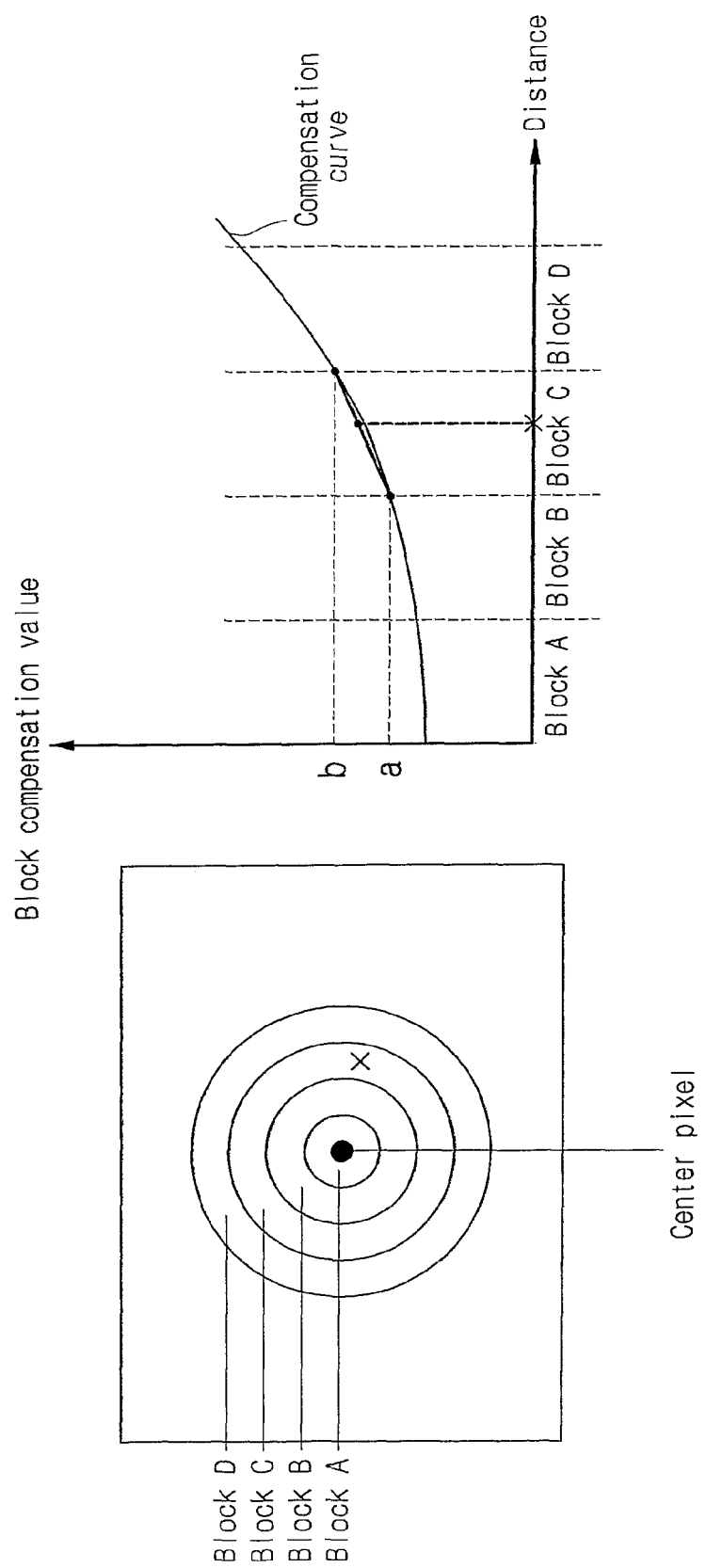
FIG. 8 is a diagram illustrating the method of calculating the compensation value for a block according to a preferred embodiment of the invention.
Figure 9:
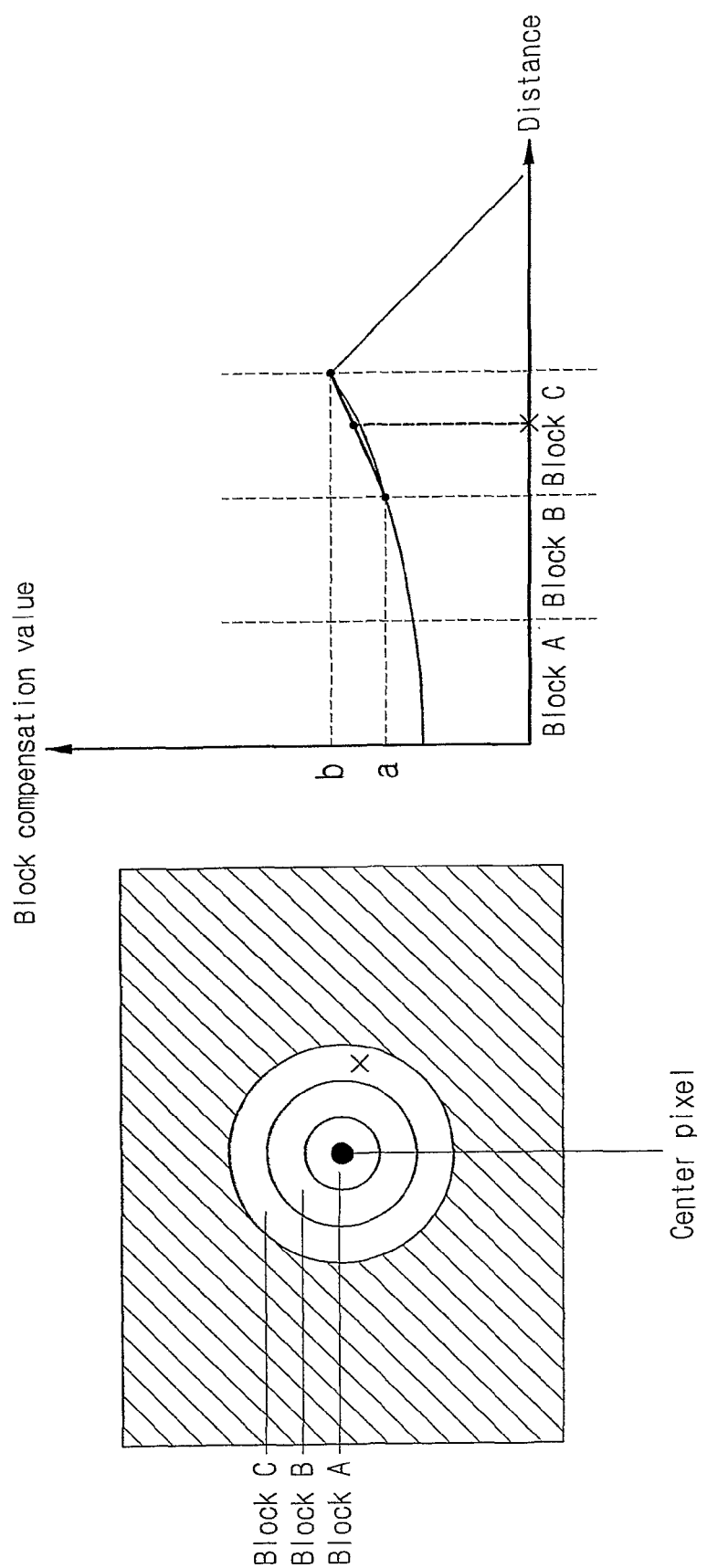
FIG. 9 is a diagram illustrating the method of implementing an image effect according to a preferred embodiment of the invention.
Figure 11:
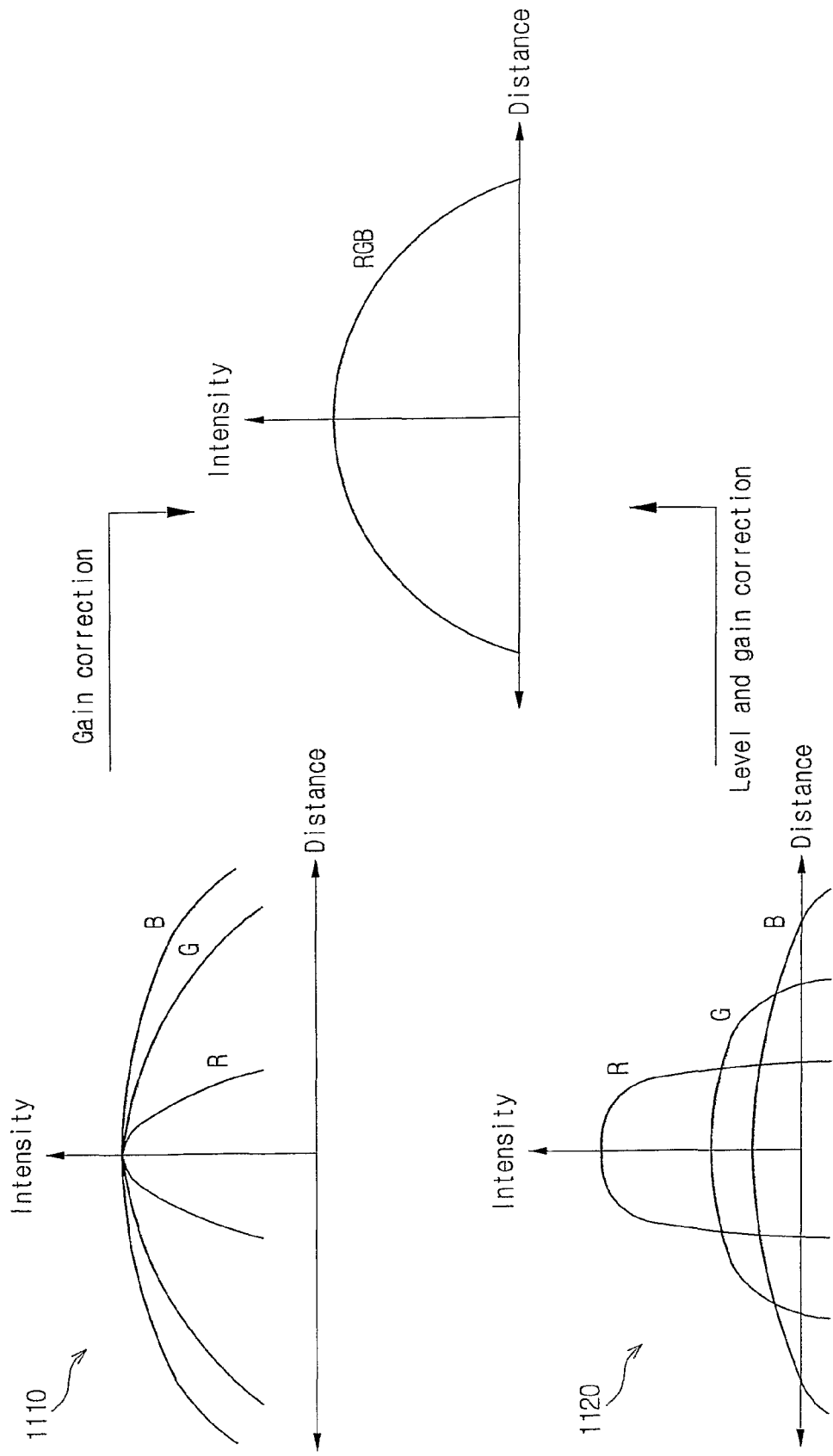
FIG. 11 is a diagram illustrating in detail the method of adjusting level and gain according to a preferred embodiment of the invention.
Figure 12:
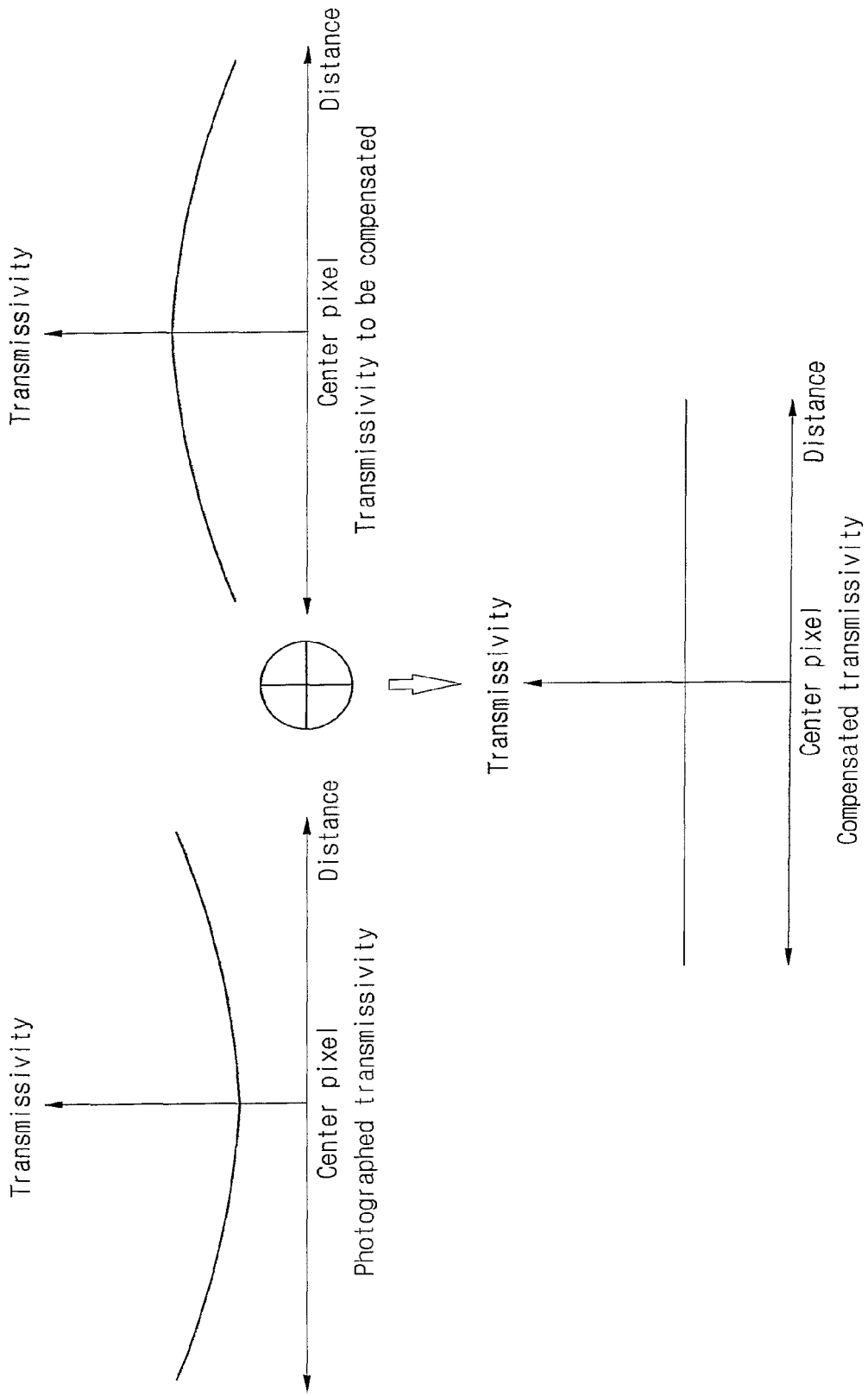
FIG. 12 is a diagram illustrating the method of providing leveled transmissivity according to a preferred embodiment of the invention.

FIG. 6 is a flowchart illustrating the method of compensating the lens shading phenomenon according to a preferred embodiment of the invention, FIG. 7 is a diagram illustrating by example a white image and a corrected image according to a preferred embodiment of the invention, and FIG. 8 is a diagram illustrating the method of calculating the compensation value for a block according to a preferred embodiment of the invention. FIG. 9 is a diagram illustrating the method of implementing an image effect according to a preferred embodiment of the invention, FIG. 10 is a diagram illustrating the method of adjusting level and gain according to a preferred embodiment of the invention, FIG. 11 is a diagram illustrating in detail the method of adjusting level and gain according to a preferred embodiment of the invention, and FIG. 12 is a diagram illustrating the method of providing leveled transmissivity according to a preferred embodiment of the invention.

Referring to FIG. 6, in step 310, the correction processing part 130 receives compensation reference value (i.e. gain and level settings) as input from the user and stores them. The user may input compensation reference value by selecting compensation standards from various compensation standard options, or may freely input compensation reference value for individual categories.

The pixel value analysis part 210 in step 320 receives from the sensor 110 digital image signals corresponding to a white image, which is from photographing a white area. The digital image signals inputted in step 320 corresponding to a white image has shading image properties, where the farther away a point is from the center of the photograph plane, the darker it becomes, due to the geometric characteristics of the lens (see 610 of FIG. 7).

The pixel value analysis part 210 in step 330 analyzes the center position of the shading image using digital image signals received per line, analyzes the luminance value, gain value, and level value for each pixel, and generates analysis data.

The pixel value analysis part 210 or the table generator part 220 in step 340 uses the analysis data and compensation reference value to generate compensation values for each pixel or for each line. Also, the generated compensation values and/or analysis data are stored in the correction register table 135. As described above, the compensation values are stored to be coupled with the count numbers corresponding to the digital image signals inputted from the horizontal and vertical directions.

In step 350, the pixel position calculator part 230 uses the count numbers, which indicate the position of each pixel, to calculate the distance between each pixel and the center pixel.

In step 360, the compensation curve generator part 240 extracts a table entry from the correction register table 135 stored to be coupled with a count number (for example, the compensation values of the starting and ending positions of the block in which the pixel is located) and calculates the compensation value corresponding to the pixel. As illustrated in FIG. 8, if the pixel to be corrected is located in block C, the compensation curve generator part 240 extracts the table entry for the starting position of block C (i.e. compensation value a) and the table entry for the ending position of block C (i.e. compensation value b) from the correction register table 135. Then, after generating a linear equation by connecting the two extracted compensation values with a straight line, the value of the linear equation corresponding to the distance of the pixel is determined as the compensation value. In calculating the compensation value, either course may be applied of making the image brighter or darker. That is, since the user may change the table entries to result either a positive or negative slope, an image with a brighter or darker perimeter may be created.

Also, as illustrated in FIG. 9, the correction processing part 130 according to the invention may implement an imaging effect of creating a circular border around the image. In addition, the image may be processed to be brighter or darker per block, or an effect of a circle spreading out in the image may be implemented.

Then, in step 370, the correction execution part 250 aggregates the analysis data of step 330 and the calculated compensation values of step 360 to generate correction pixel data, and proceeds to step 380, where it transfers the generated correction pixel data to the interpolation processing part 140.

Although it is not shown in FIG. 6, it is obvious that steps 350 to 370 may be repeated for all pixels within the frame.

As described above, the correction processing part 130 according to the invention can generate an image in which the shading phenomenon is corrected, by carefully adjusting the gain and level for RGB, respectively. The image in which the shading phenomenon is corrected is illustrated in 620 of FIG. 7. The correction processing part 130 can not only adjust gain to the decimal point level, but it can adjust level in either the positive or negative directions (see FIG. 10). The method of adjusting level and gain is described briefly with reference to FIG. 11. Generally, the RGB intensities are not equal. However, the RGB intensities are generally equal at the position of the center pixel 1110, but according to the characteristics of the lens, the RGB intensities may be unequal even at the position of the center pixel 1120. In this case, the correction processing part 130 according to the invention may provide adjustment by gain compensation when the center values of the pixel array center are equal for the respective RGB components but the respective values of peripheral pixels are different 1110, and may provide modification by level and gain compensation when the respective values are different for both the center values of the pixel array center and the values of peripheral pixels 1120.

Thus, the user may utilize a corrected image in which the transmissivity is leveled through gain adjustment for adjusting the slope of the compensation curve and through level adjustment for adjusting the level of the compensation curve (see FIG. 12).

The drawings and descriptions of the invention are for examples, being used only to explain the invention, and are not used to limit the scope of the invention as stated in the claims. Therefore, it is to be understood that various modified or unmodified embodiments may be derived from the invention by those skilled in the art. Hence, the true spirit and scope of the invention are defined by the accompanying claims only.

INDUSTRIAL APPLICABILITY

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The terminology used in the description of the invention herein is for the purpose of describing particular embodiments only and is not intended to be limiting of the invention. As used in the description of the embodiments of the invention and the appended claims, the singular forms "a" "an" and "the" are intended to include the lural forms as well unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that relative teens are intended to encompass different orientations of the device in addition to the orientation depicted in the Figures.

Moreover, it will be understood that although the terms first and second are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, and similarly, a second without departing from the teachings of the present invention.

It will also be understood that when an element is referred to as being "connected" or "coupled" to another element, it can be directly connected or coupled to the other element or intervening elements may be present. In contrast when an element is referred to as being "directly connected" or "directly coupled" to another element, there are no intervening elements present. Further, as used herein the term "plurality" refers to at least two elements. Additionally, like numbers refer to like elements throughout.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. Section 112, sixth paragraph, unless the element is expressly recited using the phrase "means for" or, in the case of a method claim, the element is recited using the phrase "step for."

As described above, the method and apparatus for compensating the lens shading phenomenon in image sensor can prevent the degradation of quality in original images.

Also, the invention can provide overall illumination compensation and compensation for the color distortion of the respective color filters of RGB and the reduction in signal amplitude according to pixel position.

Also, the invention can maintain colors as close as possible to the original through the respective compensation of RGB which takes into consideration the respective characteristics of the color filters and through the respective compensation of gain and level for the disparity in transmissivity according to position.

Further, the invention can minimize the amount of data to be processed when correcting the original image.

In addition, the invention can correct the position of the center pixel of the shading image.

The invention claimed is:

1. A method of compensating a lens shading phenomenon, the method comprising:
   capturing, by a sensor, an image;
   determining, by a correction processing part, block compensation values based, at least in part, upon a plurality of ranges of distance from a center pixel of at least a portion of the captured image to other pixels of the captured image, the determining including:
   (a) calculating a distance from the center pixel of at least a portion of the captured image to a compensation target pixel;
   (b) calculating a compensation value corresponding to the compensation target pixel using a block compensation value corresponding to the calculated distance; and
   (c) generating correction pixel data based, at least in part, upon the calculated compensation value,
   wherein the step (b) comprises:
   selecting a block corresponding to the calculated distance,
   extracting at least two compensation values corresponding to the selected block,
   generating a linear equation which passes the at least two compensation values and has distance as a variable,
   calculating the compensation value corresponding to the calculated distance using the linear equation, and
   the compensation value is determined based, at least in part, upon an analysis data corresponding to each pixel and the analysis data is determined based at least in part, upon a gain value and a level value for the pixel,
   wherein the block compensation values for RGB respectively are calculated, by using a compensation curve generator part, using a setting for a gain when degrees of intensity are equal for the RGB of the center pixel, and the block compensation values for RGB respectively are calculated using settings for a level and the gain when degrees of intensity are unequal for the RGB of the center pixel.

2. The method as set forth in claim 1, further comprising outputting the correction pixel data to an interpolation part.

3. The method as set forth in claim 1, further comprising identifying, by the correction processing part, the center pixel using digital image signals received sequentially in correspondence to each pixel from a sensor, wherein the digital image signals are Bayer pattern image signals.

4. The method as set forth in claim 3, wherein the block compensation values are generated, by the correction processing part, based mainly on a luminance component with a green (G) pixel as the standard.

5. The method as set forth in claim 1, wherein the center pixel is identified, by the correction processing part, by first detecting positions of two pixel values with highest brightness values on vertical and horizontal lines passing a pixel, and then, by using deviations between the positions of the pixel values and a position of the center value of a pixel array, moving a center of the pixel array to the center of the shading image corresponding to the at least a portion of the captured image.

6. A method of compensating a lens shading phenomenon, the method comprising:
   capturing, by a sensor, an image;
   generating, by a table generator part, a correction register table, the correction register table including a plurality of block compensation values based, at least in part, upon a plurality of ranges of distance from a center pixel to other pixels of the image; and
   compensating, by a correction processing part, a lens shading degradation of a subsequent image based in part on the correction register table, the compensating comprising:
   (a) calculating a distance from a compensation target pixel to the center pixel, and
   (b) calculating a compensation value corresponding to the compensation target pixel using a block compensation value corresponding to the distance,
   wherein the step (b) comprises:
   selecting a block corresponding to the distance,
   extracting two compensation values corresponding to the selected block,
   generating a linear equation which passes the two compensation values and has distance as a variable, and
   calculating the compensation value corresponding to the distance using the linear equation, and
   storing, by the correction processing part, a compensation reference value, the compensation reference value being a setting for a level and a gain, wherein the plurality of block compensation values are generated based, at least in part, upon the compensation reference value and analysis data of starting and ending positions of each block, respectively, and the analysis data is generated based in part upon luminance, gain and level values of each pixel, and
   the plurality of block compensation values for RGB respectively are calculated, by using a compensation curve generator part, using a setting for the gain when degrees of intensity are equal for the RGB of the center pixel, and the plurality of block compensation values for RGB respectively are calculated using settings for the level and the gain when the degrees of intensity are unequal for the RGB of the center pixel.

7. The method as set forth in claim 6, wherein the generating of the correction register table comprises:
   determining a radius increment for the plurality of ranges of distance; and
   generating the correction register table based in part on at least a luminance component of the image.

8. The method as set forth in claim 6, wherein the compensating of a lens shading degradation of a subsequent image based in part on the correction register table further comprising:
   (c) generating a correction pixel data by aggregating analysis data and the compensation value corresponding to the compensation target pixel; and
   (d) outputting the correction pixel data to an interpolation part.

9. The method as set forth in claim 8, wherein the steps (a) to (d) are sequentially performed with regard to each pixel received sequentially.

10. The method as set forth in claim 6, further comprising identifying, by the correction processing part, the center pixel using digital image signals received sequentially in correspondence to each pixel from a sensor, wherein the digital image signals are Bayer pattern image signals.

11. The method as set forth in claim 10, wherein the plurality of block compensation values are generated, by the correction processing part, based mainly on a luminance component with a green (G) pixel as the standard.

12. The method as set forth in claim 6, wherein the center pixel is identified, by the correction processing part, by first detecting positions of two pixel values with highest brightness values on vertical and horizontal lines passing a pixel, and then, by using deviations between the positions of the two pixel values and a position of the center value of a pixel array, moving the center of the pixel array to a center of a shading image corresponding to the image.

13. A method of compensating a lens shading phenomenon, the method comprising:
    capturing, by a sensor, an image;
    sampling, by a correction processing part, a pixel value from the image;
    determining, by a table generator part, a correction register table, the correction register table including a plurality of block compensation values based, at least in part, upon a plurality of ranges of distance from a center pixel to other pixels of the image;
    determining, by the correction processing part, a block compensation value based on the correction register table; and
    applying, by the correction processing part, the block compensation value to the pixel, wherein the block compensation value is calculated by a set of procedures comprising:
    selecting a block corresponding to the distance,
    extracting two compensation values corresponding to the selected block,
    generating a linear equation which passes the two compensation values and has distance as a variable, and
    calculating the block compensation value corresponding to the distance using the linear equation,
    wherein a compensation reference value is stored, by the correction processing part, the compensation reference value being a setting for a level and a gain, wherein the plurality of block compensation values are generated based, at least in part, upon the compensation reference value and analysis data of starting and ending positions of each block, respectively, and the analysis data is generated based in part upon luminance, gain and level values of each pixel, and
    wherein the plurality of block compensation values for RGB respectively are calculated, by using a compensation curve generator part, using the setting for the gain when degrees of intensity are equal for the RGB of the center pixel, and the plurality of block compensation values for RGB respectively are calculated using settings for the level and the gain when the degrees of intensity are unequal for the RGB of the center pixel.

14. An apparatus for compensating a lens shading degradation, the apparatus comprising:
    an image sensor, the image sensor capturing an image; and
    an image processor coupled to the image sensor, the image processor compensating the lens shading degradation of the image based in part upon a correction register table, the correction register table including a plurality of block compensation values based, at least in part, upon a plurality of ranges of distance from a center pixel to other pixels of the image, wherein the image processor comprises:
    a correction processing part, the correction processing part identifying the center pixel of the image using digital image signals received sequentially in correspondence to each pixel from the image sensor, the correction processing part calculating a distance from a compensation target pixel to the center pixel, the correction processing part calculating a compensation value corresponding to the compensation target pixel using a block compensation value corresponding to the distance, and the correction processing part compensating the lens shading degradation of a subsequent image based in part on the correction register table, and
    in the image processor, the block compensation value corresponding to the distance between the compensation target pixel and the center pixel is calculated by a set of procedures comprising:
    selecting a block corresponding to the distance,
    extracting two compensation values corresponding to the selected block,
    generating a linear equation which passes the two compensation values and has distance as a variable, and
    calculating the compensation value corresponding to the distance using the linear equation,
    wherein a compensation reference value is stored in the image processor, the compensation reference value is a setting for a level and a gain, wherein the plurality of block compensation values are generated based, at least in part, upon the compensation reference value and analysis data of starting and ending positions of each block, respectively, and the analysis data is generated based in part upon luminance, gain and level values of each pixel, and
    wherein the plurality of block compensation values for RGB respectively are calculated, by the compensation curve generator part, using the setting for the gain when degrees of intensity are equal for the RGB of the center pixel, and the plurality of block compensation values for RGB respectively are calculated using settings for the level and the gain when the degrees of intensity are unequal for the RGB of the center pixel.

15. An apparatus for compensating a lens shading degradation, the apparatus comprising:
    an image sensor, the image sensor capturing an image; and
    means for generating a correction register table including a plurality of block compensation values based, at least in part, upon a plurality of ranges of distance from a center pixel to other pixels of the image;
    means for generating a compensation value corresponding to the distance between the other pixels and the center pixel by a set of procedures comprising:
    selecting a block corresponding to the distance,
    extracting two compensation values corresponding to the selected block,
    generating a linear equation which passes the two compensation values and has distance as a variable, and
    calculating the compensation value corresponding to the distance using the linear equation;
    means for compensating the lens shading degradation of a subsequent image based in part on the correction register table,
    wherein a compensation reference value is stored, by the means for generating, the compensation reference value is a setting for a level and a gain, wherein the plurality of block compensation values are generated based, at least in part, upon the compensation value and analysis data of starting and ending positions of each block, respectively, and the analysis data is generated based in part upon luminance, gain and level values of each pixel, and wherein the plurality of block compensation values for RGB respectively are calculated, by using a compensation curve generator part, using a setting for the gain when degrees of intensity are equal for the RGB of the center pixel, and the plurality of block compensation values for RGB respectively are calculated using settings for the level and the gain when the degrees of intensity are unequal for the RGB of the center pixel.

* * * * *